United States Patent
Loffler et al.

(10) Patent No.: US 6,179,768 B1
(45) Date of Patent: Jan. 30, 2001

(54) CAPSULE FOR USE IN BRACHYTHERAPY AND A COMBINATION OF A CAPSULE FOR BRACHYTHERAPY AND A GUIDEWIRE

(75) Inventors: Edgar German Loffler, Kleve (DE); Arie Luite Visscher, Driebergen (NL)

(73) Assignee: Delft Instruments Intellectual Property B.V. (NL)

( * ) Notice: Under 35 U.S.C. 154(b), the term of this patent shall be extended for 0 days.

(21) Appl. No.: 09/214,428
(22) PCT Filed: Jul. 7, 1997
(86) PCT No.: PCT/NL97/00389
    § 371 Date: Mar. 3, 1999
    § 102(e) Date: Mar. 3, 1999
(87) PCT Pub. No.: WO98/01186
    PCT Pub. Date: Jan. 15, 1998

(30) Foreign Application Priority Data

Jul. 8, 1996 (NL) ................................... 1003543

(51) Int. Cl.[7] .............. A61M 36/00; A61M 5/00
(52) U.S. Cl. ...................................................... 600/7
(58) Field of Search .............................. 600/1–8

(56) References Cited

U.S. PATENT DOCUMENTS 4,323,055   4/1982  Kubiatowicz .
4,861,520   8/1989  Van't Hooft et al. .
5,688,220 * 11/1997 Verin et al. ............................. 600/1

FOREIGN PATENT DOCUMENTS

90/01208   2/1990  (WO) .

* cited by examiner

*Primary Examiner*—Max Hindenburg
*Assistant Examiner*—Brian Szmal
(74) *Attorney, Agent, or Firm*—Birch, Stewart, Kolasch & Birch LLP

(57) ABSTRACT

A capsule for taking up at least one radioactive source for application in brachytherapy and to be connected to a guidewire, the capsule having a cylindrical mantle that can be closed on the proximal end by a coupling element, and the capsule having a rounded top section at its distal end, the mantle and the inner surface of the top section defining a substantially straight circular-cylindrical cavity, in which the operation at least one radioactive source is placed, the inner surface of the top section, at least in a peripheral area thereof, being curved in distal direction and the cavity continuing somewhat in the top section, and the end of that least one radioactive source, which is located near the inner surface of the top section, is finished in a complementary curved fashion.

12 Claims, 1 Drawing Sheet

US 6,179,768 B1

CAPSULE FOR USE IN BRACHYTHERAPY AND A COMBINATION OF A CAPSULE FOR BRACHYTHERAPY AND A GUIDEWIRE

The invention relates to a capsule for taking up at least one radioactive source for application in brachytherapy and to be connected to a guidewire, the capsule having a cylindrical mantle that can be closed on the proximal end by means of a coupling element, and the capsule having a rounded top section at its distal end, and the mantle and the inner surface of the top section defining a substantially straight circular-cylindrical cavity, in which in operation at least one radioactive source is placed.

The invention also relates to a combination of a guide-wire and such a capsule.

BACKGROUND OF THE INVENTION

Such a combination as described above, is known in practice and described, for instance, in U.S. Pat. No. 4,861,520, which is herewith incorporated by reference.

For local radioactive radiation treatment of a specific internal area of the human body, such as a tumor, or a wall section of a blood vessel, it is possible, as described in U.S. Pat. No. 4,861,520, to deliver a capsule with a radioactive source, via a tubular guiding device, such as, for instance, a hollow needle, a flexible tube or a catheter or the like, to the area to be treated. For this purpose, normally the so-called "after loading" technique is employed. First, the catheter or the like is placed in the body and then the capsule attached to the distal end of a guidewire is delivered with the help of a remotely controlled device to the treatment area (referred to as brachytherapy).

In order to deliver the capsule to the area to be treated in a reliable and safe manner via the tubular guiding device, even when the tubular guiding device is forming sharp curves, the capsule should be as short as possible and its front have a smooth shape without sharp transitions.

In the combination known from U.S. Pat. No. 4,861,520, the capsule has at the front, that is to say the end facing away from the guidewire, a closed, almost semi-spherical solid end that forms a whole together with the cylindrical mantle of the capsule. At the end facing the guidewire, the connection between the capsule and the guidewire is formed by a connecting device (coupling element), partly extending in the cylindrical mantle and connected through welding to the distal end of the guidewire and the cylindrical mantle. This makes possible a considerably shorter capsule with regard to the prior art, according to which the cylindrical mantle was provided at the front with a solid plug extending partly in the cylindrical mantle with a semi-spherical end. The obtained length advantage was on the order of 25% with the application of seven miniature radioactive source elements. With a conventional capsule with an original length of 7.2 mm and a diameter of 1.1 mm, a length reduction to a length of 5.5 mm was realized.

A problem with the known combination is that the wall thickness of the capsule in front at the place of the semi-spherical end is greater than that at the place of the cylindrical mantle. Thus, the capsule is still longer than necessary. Moreover, the greater wall thickness in the distal end of the capsule disturbs the radiation pattern, since, viewed from the source, more radiation is absorbed in the axial direction than in the radial direction.

SUMMARY OF THE INVENTION

The invention intends to remove the outlined problem and in general make available an improved capsule for brachytherapy. For this purpose, according to the invention, a capsule with the described type is characterized in that the inner surface of the top section, at least in a peripheral area thereof, is curved in distal direction, and in that the cavity continues somewhat in the top section, and that the end of the at least one radioactive source, which is located near the inner surface of the top section, is finished in a complementary curves fashion.

BRIEF DESCRIPTION OF THE DRAWINGS

The invention will be described in more detail in the following, with reference to the attached drawing.

DESCRIPTION OF PREFERRED EMBODIMENTS

Figure 1:
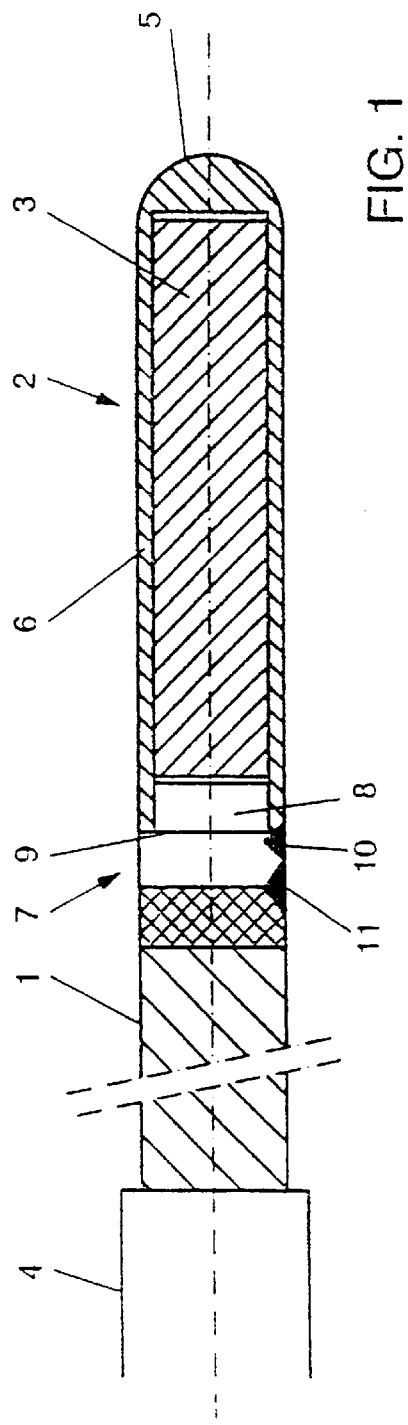
FIG. 1 shows schematically a longtudinally cross-sectional diagram of an example of a guidewire with a capsule provided With a radiation source according to the prior art.

FIG. 1 shows a cross-sectional diagram of an example of a guidewire 1 that is provided at its distal end with a capsule 2 for one or more radiation sources 3. The proximal end of the guidewire is provided with coupling means 4 or the like, in order to operate the guidewire. The capsule is closed at its distal end and has there a semi-spherical top section 5. From the top section 5, a cylindrical mantle 6 extends backward. The proximal end of the mantle is sealed with a solid coupling element 7 that has a part 8 extending in the mantle, with a reduced diameter, and a part 9, located in the extension of the mantle, having a diameter essentially the same as the mantle. The coupling element 7 is connected preferably through welding, for instance, laser welding, with both the guidewire 1 and the mantle 6. Such welds are indicated schematically at 10 and 11. The capsule 2 has in longitudinal cross-section an elongate rectangular cavity bounded by the top section, the mantle, the coupling element and the inner surface of the top section in which one or more radiation sources may be placed. In the example shown, a single rod-shaped radiation source, for example a small Iridium rod, is applied having also a rectangular shape.

FIG. 1 clearly shows that the semi-spherical top section of the capsule forms a much thicker wall section than the mantle. Thus, viewed from the source, radiation emitted in the axial direction is absorbed to a higher degree than radiation emitted in the radial direction so that near the front end of the capsule, an irregular radiation pattern occurs.

FIG. 2 again shows an example of a combination according to the invention. FIG. 2 again shows a capsule 20 for incorporating one or more radiation sources 21 for brachytherapy. As an example, it is shown that the capsule may be connected, if desired, although not necessary, via a short thin cable or thread 22 with the guidewire 1, which normally and substantially has the same diameter as the capsule. The coupling element 23 has a shape adapted thereto. A combination with a thin cable or thread between the capsule and the guidewire is described in the related Dutch patent application No. 1003528.

Figure 2:
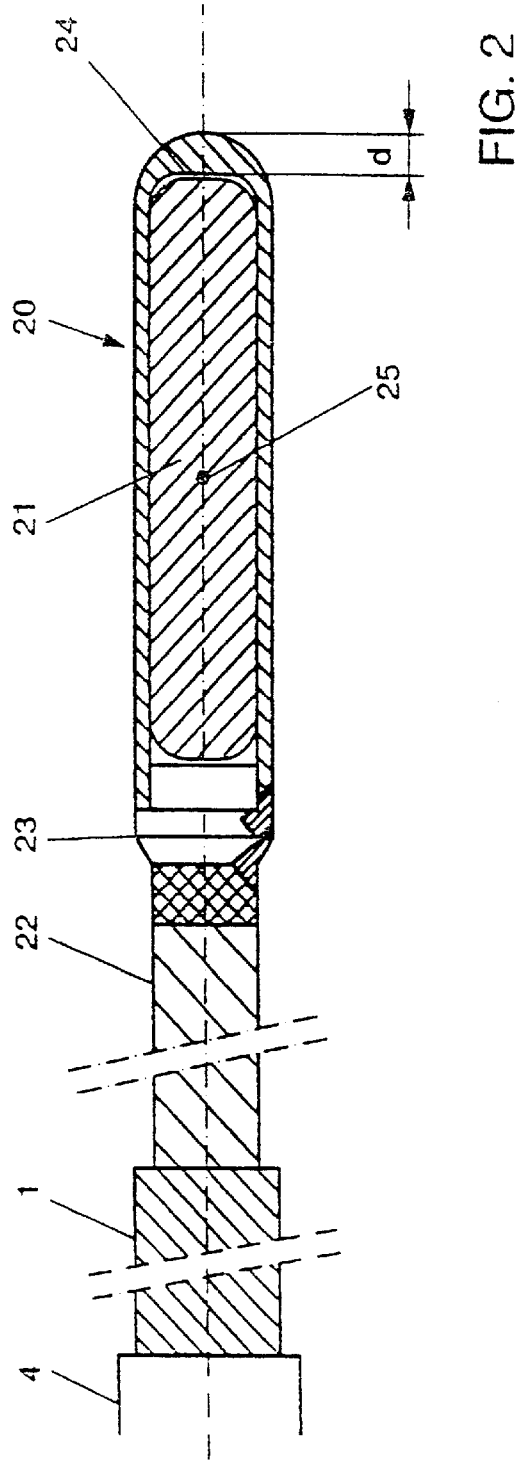
FIG. 2 shows schematically a longtudinally cross-sectional diagram of an example of a combination of a guidewire (partially shown) and a capsule with a radiation source according to the invention.

The capsule 20 in FIG. 2 differs from the capsule shown in FIG. 1 in that the end surface 24 of the cavity in the capsule, i.e., the inner surface of the top section, has, at least in the area along the periphery of the end surface, a certain curvature, which viewed from the cavity extends outward to the top. Thus, the distance "d" between the top of the capsule and the center of the end surface is considerably less than is the case with the known capsule. By implementing the rod-shaped radiation source 21, or in the case of several radiation sources, the front radiation source, with an adapted convex end surface, the distance between the front end of the capsule and the radiation center of gravity 25 may be reduced, as well.

A further improvement is possible by flattening the top section of the capsule somewhat.

A combination with a capsule according to the invention therefore provides an improved radiation pattern and, moreover, makes a shorter capsule possible.

It should be noted that according to the abovementioned, various modifications are obvious to a person skilled in the art. For instance, the at least one radiation source nay be curved at the other end in a corresponding manner. This especially provides an advantage if a single rod-shaped source is applied.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. In a capsule for containing at least one radioactive source for application in brachytherapy and connected to a guidewire, the capsule comprising a cylindrical mantle closed at a proximal end by a coupling element, the capsule having a rounded top section at its distal end, and the mantle and an inner surface of the top section define a substantially straight circular-cylindrical cavity, in which in operation at least one radioactive source is placed, the inner surface of the top section at least in a peripheral area thereof being curved in a distal direction, the cavity continued into the top section, and an end of the at least one radioactive source which is located near the inner surface of the top section being finished in a complementary curved fashion.

2. The capsule according to claim 1, wherein the top section of the capsule is flattened on the outside.

3. A combination of a guidewire with a capsule according to claim 1.

4. The combination according to claim 3, wherein between the capsule and the guidewire, a relatively short thread or cable with reduced diameter is provided.

5. The combination according to claim 3, wherein the at least one radioactive source is a single rod-shaped radiation source having a curved shape at both ends the single radiation source being contained in the capsule.

6. The combination according to claim 3, wherein the guidewire is fixedly attached to the capsule.

7. The combination according to claim 4, wherein the guidewire is fixedly attached to the short thread or cable.

8. The combination according to claim 7, wherein the short thread or cable is fixedly attached to the capsule.

9. The capsule according to claim 1, wherein the curved end of the at least one radioactive source lies beneath the curved area of the inner surface of the top section of the capsule.

10. The capsule according to claim 1, wherein a plane passing through a tip of the curved end of the at least one radioactive source intersects the curved area of the inner surface of the top section of the capsule provided the plane is perpendicular to a longitudinal axis of the capsule.

11. The capsule according to claim 1, further comprising means for providing a uniform radiation pattern at the distal end of the capsule, the means includes the rounded top section of the capsule, the curved inner surface of the capsule and the curved end of the at least one radioactive source.

12. The capsule according to claim 1, wherein the at least one radioactive source is a single rod-shaped radiation source having a curved shape at both ends.

\* \* \* \* \*